United States Patent [19]
Okamoto et al.

[11] Patent Number: 5,856,568
[45] Date of Patent: Jan. 5, 1999

[54] PROCESS FOR INHIBITING POLYMERIZATION OF A VINYL COMPOUND

[75] Inventors: Kenji Okamoto; Takashi Nakagawa; Kouji Tomita, all of Tokuyama, Japan

[73] Assignee: Idemitsu Petrochemical Co., Ltd., Tokyo, Japan

[21] Appl. No.: 849,072

[22] PCT Filed: Sep. 20, 1996

[86] PCT No.: PCT/JP96/02708

§ 371 Date: May 30, 1997

§ 102(e) Date: May 30, 1997

[87] PCT Pub. No.: WO97/12851

PCT Pub. Date: Apr. 10, 1997

[30] Foreign Application Priority Data

Oct. 2, 1995 [JP] Japan ................. 7-254930
Jan. 18, 1996 [JP] Japan ................. 8-006388

[51] Int. Cl.$^6$ .................. C07C 57/02; C07C 57/04
[52] U.S. Cl. .................. 562/598; 562/599; 562/600
[58] Field of Search .................. 562/598, 599, 562/600

[56] References Cited

U.S. PATENT DOCUMENTS 4,980,079 12/1990 Yamato et al. .................. 252/180
5,034,156 7/1991 Varwig .................. 252/403
5,292,920 3/1994 Upmacis et al. .................. 560/4
5,504,243 4/1996 Sakamoto et al. .................. 560/205

FOREIGN PATENT DOCUMENTS 6-211735  8/1994  Japan .

Primary Examiner—Gary Geist
Assistant Examiner—Rosalynd Keys
Attorney, Agent, or Firm—Oblon, Spivak, McClelland, Maier & Neustadt, P.C.

[57] ABSTRACT

A process for inhibiting polymerization of a vinyl compound comprising using (A) one or both of N-nitrosophenylhydroxylamine and a salt thereof in combination with (B) a salt of copper or in combination with (B') a metal salt of a dialkyldithiocarbamic acid and (C) at least one selected from the group consisting of inorganic acids, salts of inorganic acids, and water.

In accordance with the above process, stable continuous operation of a process for producing a vinyl compound, particularly acrylic acid or methacrylic acid, such as a distillation process of the vinyl compound, for a long time is enabled by effectively suppressing polymerization of the vinyl compound in the process or by effectively suppressing polymerization of the vinyl compound in the process while corrosion of the apparatus for the production is prevented.

21 Claims, No Drawings

PROCESS FOR INHIBITING POLYMERIZATION OF A VINYL COMPOUND

TECHNICAL FIELD

The present invention relates to a process for inhibiting polymerization of a vinyl compound. More particularly, the present invention relates to a process for inhibiting polymerization of a vinyl compound which enables stable continuous operation of a process for producing a vinyl compound, particularly acrylic acid or methacrylic acid, such as a distillation process of the vinyl compound, for a long time by effectively suppressing polymerization of the vinyl compound in parts of the liquid phase and in parts formed by condensation of the gaseous phase in the process or by effectively suppressing polymerization of the vinyl compound in parts of the liquid phase and in parts formed by condensation of the gaseous phase in the process while corrosion of the apparatus for the production is prevented.

BACKGROUND ART

It has heretofore been known that vinyl compounds, such as styrene, acrylic acid, methacrylic acid, esters of acrylic acid, esters of methacrylic acid, and acrylonitrile, are easily polymerized by light or heat. In processes for producing vinyl compounds, various types of distillation are conducted for separation and recovery, concentration, or purification of the desired vinyl compounds. However, because vinyl compounds form polymeric materials by polymerization by light or heat as described above, various problems arise in the distillation process and cause various undesirable phenomena, such as that a stable continuous operation for a long time is made impossible.

Therefore, distillation operation has heretofore been conducted in the presence of a polymerization inhibitor in order to avoid these problems caused by polymerization in the distillation process. As the polymerization inhibitor, for example, copper dibutyldithiocarbamate, hydroquinone, methoquinone (p-methoxyphenol), p-t-butylcatechol, t-butylhydroquinone, or phenothiazine is used. However, these polymerization inhibitors exhibit small or very limited effect to inhibit polymerization in parts formed by condensation of the gaseous phase although a relatively desirable effect is exhibited in parts of the liquid phase. Therefore, the problem that, in a distillation tower, formation of polymerized materials cannot be suppressed in parts where the fluid containing a polymerization inhibitor is not sufficiently supplied has persisted. There has also been another problem that copper dibutyldithiocarbamate described above cannot readily be used in an industrial plant because this compound corrodes apparatus, such as those made of SUS 316.

On the other hand, a process for inhibiting polymerization of acrylic acid by using a cobalt, nickel, or manganese complex of N-nitrosophenylhydroxylamine has been proposed (the specification of the U.S. Pat. No. 4,638,079. However, this process has a drawback in that the effect of inhibiting polymerization is not sufficiently exhibited in a system containing both of the gaseous phase and the liquid phase, such as the distillation process of acrylic acid.

DISCLOSURE OF THE INVENTION

Under the above circumstances, the present invention has the object of providing a process for inhibiting polymerization of a vinyl compound which enables stable continuous operation of a process for producing a vinyl compound, particularly acrylic acid or methacrylic acid, such as a distillation process of the vinyl compound, for a long time by effectively suppressing polymerization of the vinyl compound in parts of the liquid phase and in parts formed by condensation of the gaseous phase in the process or by effectively suppressing polymerization of the vinyl compound in parts of the liquid phase and in parts formed by condensation of the gaseous phase in the process while corrosion of the apparatus for the production is prevented.

As the result of extensive studies undertaken by the present inventors to achieve the above object, it was discovered that an excellent effect of inhibiting polymerization is exhibited in both of parts of the liquid phase and parts formed by condensation of the gaseous phase when N-nitrosophenylhydroxylamine or a salt thereof is used in combination with a salt of copper, particularly copper dibutyldithiocarbamate, as the polymerization inhibitor. It was also discovered that an excellent effect of inhibiting polymerization is exhibited in both of parts of the liquid phase and parts formed by condensation of the gaseous phase and, at the same time, corrosion of the apparatus can effectively be suppressed when N-nitrosophenylhydroxylamine or a salt thereof is used in combination with a metal salt of a dialkyldithiocarbamic acid, particularly copper dibutyldithiocarbamate, as the polymerization inhibitor, and an inorganic acid, a salt of an inorganic acid, or water is used as the agent for suppressing corrosion. The present invention has been completed on the basis of the discoveries.

Accordingly, the present invention provides:
(1) A process for inhibiting polymerization of a vinyl compound comprising using (A) one or both of N-nitrosophenylhydroxylamine and a salt thereof in combination with (B) a salt of copper (Invention 1); and
(2) A process for inhibiting polymerization of a vinyl compound comprising using (A) one or both of N-nitrosophenylhydroxylamine and a salt thereof in combination with (B') a metal salt of a dialkyldithiocarbamic acid and (C) at least one selected from the group consisting of inorganic acids, salts of inorganic acids, and water (Invention 2).

THE MOST PREFERRED EMBODIMENT TO CARRY OUT THE INVENTION

Examples of the vinyl compound to which the process of the present invention can be applied include styrene, acrylic acid, methacrylic acid, esters of acrylic acid, esters of methacrylic acid, and acrylonitrile. Among these vinyl compounds, acrylic acid and methacrylic acid are preferable.

In Invention 1 and Invention 2, component (A) which is one or both of N-nitrosophenylhydroxylamine and a salt thereof is used as a polymerization inhibitor. N-nitrosophenylhydroxylamine used as component (A) is not particularly limited, and a commercially available material can be used. A high purity N-nitrosophenylhydroxylamine is preferable for exhibiting a superior effect. The salt of N-nitrosophenylhydroxylamine is not particularly limited, and various salts may be used. Because of the easier availability and the superior effect, ammonium salt of N-nitrosophenylhydroxylamine is particularly preferable.

In the present invention, N-nitrosophenylhydroxylamine and the salts thereof described above may be used singly or as a combination of two or more types.

In Invention 1, component (B) which is a salt of copper is used as a polymerization inhibitor in combination with one or both of N-nitrosophenylhydroxylamine and a salt thereof described above. The salt of copper is not particularly limited, and various salts including inorganic salts and organic salts may be used. Examples of the salt of copper include copper dialkyldithiocarbamates, copper acetates, copper naphthenates, copper acrylates, copper sulfates, copper nitrates, and copper chlorides. As the salt of copper, any of copper (I) salts and copper (II) salts may be used.

Among the above salts of copper, copper dialkyldithiocarbamates are preferable because of the superior effect. Examples of the copper dialkyldithiocarbamate include compounds represented by the following general formula (I):

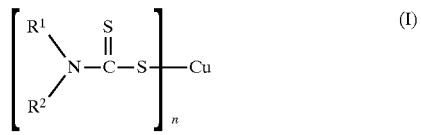

In the above general formula (I), $R^1$ and $R^2$ represents each an alkyl group having 1 to 8 carbon atoms or phenyl group. The alkyl group having 1 to 8 carbon atoms may be linear or branched. Specific examples of the alkyl group having 1 to 8 carbon atoms include methyl group, ethyl group, propyl groups, butyl groups, pentyl groups, and hexyl groups. $R^1$ and $R^2$ may be the same or different. n represents the valency of copper and 1 or 2.

Examples of the copper dialkyldithiocarbamate represented by the general formula (I) include copper dimethyldithiocarbamates, copper diethyldithiocarbamates, copper dipropyldithiocarbamates, copper dibutyldithiocarbamates, copper dipentyldithiocarbamates, copper dihexyldithiocarbamates, copper diphenyldithiocarbamates, copper methylethyldithiocarbamates, copper methylpropyldithiocarbamates, copper methylbutyldithiocarbamates, copper methylpentyldithiocarbamates, copper methylhexyldithiocarbamates, copper methylphenyldithiocarbamates, copper ethylpropyldithiocarbamates, copper ethylbutyldithiocarbamates, copper ethylpentyldithiocarbamates, copper ethylhexyldithiocarbamates, copper ethylphenyldithiocarbamates, copper propylbutyldithiocarbamates, copper propylpentyldithiocarbamates, copper propylhexyldithiocarbamates, copper propylphenyldithiocarbamates, copper butylpentyldithiocarbamates, copper butylhexyldithiocarbamates, copper butylphenyldithiocarbamates, copper pentylhexyldithiocarbamates, copper pentylphenyldithiocarbamates, and copper hexylphenyldithiocarbamates. The copper dialkyldithiocarbamate described above may be any of copper (I) salts and copper (II) salts.

Among the above copper salts, copper dimethyldithiocarbamates, copper diethyldithiocarbamates, and copper dibutyldithiocarbamates are preferable because of the superior effect and the easier availability. The salt of copper may be used singly or as a combination of two or more types.

In Invention I, polymerization of a vinyl compound is inhibited by supplying component (A) which is one or both of N-nitrosophenylhydroxylamine and a salt thereof and component (B) which is a salt of copper to a system in which the vinyl compound is present so that component (A) and component (B) are both present in the system. The description "component (A) and component (B) are both present in the system" is not limited to the condition in which one or both of N-nitrosophenylhydroxylamine and a salt thereof and the salt of copper are both present in the system while the specific chemical structures of the components are kept intact, but also include the condition in which a part or the whole of N-nitrosophenylhydroxylamine, a salt thereof, or the salt of copper is decomposed or ionized, and the condition in which a copper complex of N-nitrosophenylhydroxylamine or a salt thereof is formed.

The method of supplying the above components to the system is not particularly limited, and one or both of N-nitrosophenylhydroxylamine and a salt thereof and the salt of copper may be added to the system separately or as a mixture of one or both of N-nitrosophenylhydroxylamine and a salt thereof and the salt of copper. When one or both of N-nitrosophenylhydroxylamine and a salt thereof and the salt of copper are separately added, it is more advantageous that one or both of N-nitrosophenylhydroxylamine and a salt thereof are added to the system after the salt of copper has been added because a superior effect of inhibiting polymerization is occasionally exhibited.

In Invention I, the concentrations of the used components are as following. The concentration of component (A) which is one or both of N-nitrosophenylhydroxylamine and a salt thereof is preferably in the range of 1 ppm by weight to 10% by weight based on the amount of the vinyl compound. When the concentration is less than 1 ppm by weight, there is the possibility that the effect of inhibiting polymerization is not sufficiently exhibited. When the concentration is more than 10% by weight, the effect is not increased to the degree expected from the used amount, and the concentration causes economic disadvantage in many cases. In view of the effect of inhibiting polymerization and the economic advantage, the more preferable concentration is in the range of 5 to 1000 ppm by weight based on the amount of the vinyl compound. A concentration in the range of 10 to 500 ppm by weight is most preferable. The concentration by weight of component (B) which is the salt of copper is preferably in the range of 0.001 to 1000 times the concentration by weight of component (A) which is one or both of N-nitrosophenylhydroxylamine and a salt thereof. When the concentration is less than 0.001 times the concentration of one or both of N-nitrosophenylhydroxylamine and a salt thereof, there is the possibility that the effect of inhibiting polymerization in both of parts of the liquid phase and parts formed by condensation of the gaseous phase is not sufficiently exhibited, and it is difficult to achieve the object of the present invention. When the concentration is more than 1000 times the concentration of one or both of N-nitrosophenylhydroxylamine and a salt thereof, the effect is not increased to the degree expected from the used amount, and the concentration causes economic disadvantage. Furthermore, there is the possibility that other disadvantages arise. In view of the effect of inhibiting polymerization in both of parts of the liquid phase and parts formed by condensation of the gaseous phase and the economic advantage, the more preferable concentration by weight of the salt of copper is in the range of 0.01 to 100 times the concentration by weight of component (A) which is one or both of N-nitrosophenylhydroxylamine and a salt thereof. A concentration in the range of 0.1 to 10 times the concentration of component (A) is most preferable. When one or both of N-nitrosophenylhydroxylamine and a salt thereof and the salt of copper are present in the system in the form of a N-nitrosophenylhydroxylamine (or a salt thereof)—copper complex, the concentration of the complex is preferably in the range of 1 ppm by weight to 10% by weight, more preferably in the range of 5 to 5000 ppm by weight, most preferably 10 to 2000 ppm by weight, based on the amount of the vinyl compound in view of the effect of inhibiting polymerization in both of parts of the liquid phase and parts formed by condensation of the gaseous phase and the economic advantage.

In Invention II, component (B') which is a metal salt of a dialkyldithiocarbamic acid is used as a polymerization inhibitor in combination with component (A) described above which is one or both of N-nitrosophenylhydroxylamine and a salt thereof, and, in addition to these components, component (C) which is at least one selected from the group consisting of inorganic acids, salts of inorganic acids, and water is used as the agent for suppressing corrosion.

As the metal salt of a dialkyldithiocarbamic acid of component (B'), for example, a compound represented by the general formula (II):

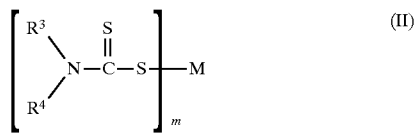

can be used.

In the above general formula (II), $R^3$ and $R^4$ represent each an alkyl group having 1 to 8 carbon atoms or phenyl group. The alkyl group having 1 to 8 carbon atoms may be linear or branched. Specific examples of the alkyl group having 1 to 8 carbon atoms include methyl group, ethyl group, propyl groups, butyl groups, pentyl groups, and hexyl groups. $R^3$ and $R^4$ may be the same or different. M represents a metal, such as nickel, zinc, copper, iron, and a transition metal such as Mn and Co. m represents the valency of the metal represented by M.

Examples of the metal salt of a dialkyldithiocarbamic acid represented by the above general formula (II) include copper dialkyldithiocarbamates represented by the general formula (I), and nickel salts, zinc salts, iron salts, and various types of transition metal salt such as Mn salts and Co salts, corresponding to the copper dialkyldithiocarbamates. Among these metal salts of dialkyldithiocarbamates, copper dialkyldithiocarbamates are preferable, and copper dibutyldithiocarbamate is more preferable, in view of the effect. Copper dibutyldithiocarbamate is easily available as a commercial product.

The above metal salt of a dialkyldithiocarbamic acid may be used singly or as a combination of two or more types. The used amount is not particularly limited, and suitably selected in accordance with the condition. The amount is generally selected in the range of 0.001 to 5% by weight based on the amount of the vinyl compound. When the amount is less than 0.001% by weight, the effect of inhibiting polymerization in parts of the liquid phase is occasionally not sufficiently exhibited. When the amount is more than 5% by weight, the effect of inhibiting polymerization is not increased to the degree expected from the used amount, and the amount causes economic disadvantage in many cases. In view of the effect of inhibiting polymerization in parts of the liquid phase and the economic advantage, the used amount of the metal salt of the dialkyldithiocarbamic acid is preferably in the range of 0.01 to 1% by weight, more preferably in the range of 0.05 to 0.5% by weight, based on the amount of the vinyl compound.

In Invention II, the used amount of component (A) which is one or both of N-nitrosophenylhydroxylamine and a salt thereof can suitably be selected. The amount by weight of component (A) is generally selected in the range of 0.01 to 10 times the amount by weight of component (B') which is the metal salt of a dialkyldithiocarbamic acid. When the amount is less than 0.01 times the amount of component (B'), the effect of inhibiting polymerization in parts formed by condensation of the gaseous phase is occasionally not sufficiently exhibited. When the amount is more than 10 times the amount of component (B'), the effect is not increased to the degree expected from the used amount, and the amount causes economic disadvantage in many cases. In view of the effect of inhibiting polymerization in parts formed by condensation of the gaseous phase and the economic advantage, the preferable amount by weight of component (A) which is one or both of N-nitrosophenylhydroxylamine and a salt thereof is in the range of 0.05 to 1 times the amount by weight of the salt of a dialkyldithiocarbamic acid.

In Invention II, component (C) which is at least one selected from the group consisting of inorganic acids, salts of inorganic acids, and water is used as the agent for suppressing corrosion to suppress corrosion of the apparatus. As the inorganic acid, oxoacids are preferable. Specific examples of the inorganic acid include boric acid, phosphoric acid, nitric acid, and sulfuric acid. Among these inorganic acids, phosphoric and boric acid are preferable, and phosphoric acid is more preferable. Examples of the salt of an inorganic acid include nickel salts, zinc salts, iron salts, manganese salts, and cobalt salts of these inorganic acids.

In the present invention, the agent for suppressing corrosion of component (C) may be used singly or as a combination of two or more types. The used amount varies depending on the condition and cannot invariably be decided. The amount is generally selected in the range of 0.001 to 5% by weight based on the amount of the vinyl compound. When the amount is less than 0.001% by weight, the effect of suppressing corrosion is occasionally not sufficiently exhibited. When the amount is more than 5% by weight, the effect is not increased to the degree expected from the amount, and there is the possibility that other disadvantages arise. In view of the effective suppression of corrosion without causing other disadvantages, the used amount of the inorganic acid or the salt of the inorganic acid is preferably in the range of 0.01 to 3% by weight, more preferably in the range of 0.03 to 1% by weight.

Specifically when phosphoric acid is used as the agent for suppressing corrosion, the used amount by weight of phosphoric acid is preferably 0.01 times or more, more preferably 0.1 to 3 times, the weight of the metal salt of a dialkyldithiocarbamic acid, particularly the copper salt of a dialkyldithiocarbamic acid, described above.

Specifically when water is used as the agent for suppressing corrosion, the used amount of water can suitably be selected. The amount of water is generally selected in the range of 0.05 to 5% by weight based on the amount of the vinyl compound. When the amount is less than 0.05% by weight, the effect of suppressing corrosion is not sufficiently exhibited. When the amount is more than 5% by weight, a large amount of energy is required for separation of water, and the economic disadvantage occasionally arises. In view of the effect of suppressing corrosion and the economic advantage, the preferable amount of water is in the range of 0.07 to 0.5% by weight based on the amount of the vinyl compound.

In Invention II, the method of supplying component (A), component (B'), and component (C) described above to a system is not particularly limited. For example, (1) a method in which component (A), component (B'), and component (C) are separately supplied; (2) a method in which a mixture solution containing component (A), component (B'), and component (C) is supplied; (3) a method in which component (C) and a mixture solution containing component (A) and component (B') are supplied; (4) a method in which component (B') and a mixture solution containing component (A) and component (C) are supplied; or (5) a method in which component (A) and a mixture solution containing component (B') and component (C) are supplied; can be used.

In method (1), it is preferred that component (A) is supplied first and component (B') and component (C) are subsequently supplied to the system in the presence of component (A). The order of supplying component (B') and component (C) is not particularly limited. In method (2), it is preferred that the mixture solution is prepared by adding component (A) and component (C) to a suitable amount of the vinyl compound which is used for the present invention, followed by adding component (B') to the resultant solution, or by adding component (A) to a suitable amount of the vinyl compound which is used for the present invention, followed by adding component (B') and component (C) to the resultant solution. In method (3), it is preferred that a mixture solution is prepared by adding component (A) to a suitable amount of the vinyl compound which is used for the present invention, followed by adding component (B') to the resultant solution, then the prepared mixture solution is supplied to the system, and component (C) is supplied to the system in the presence of component (A) and component (B'). In method (4), it is preferred that a mixture solution is prepared by adding component (A) and component (C) to a suitable amount of the vinyl compound which is used for the present invention, then the prepared mixture solution is supplied to the system, and component (B') is supplied to the system in the presence of component (A) and component (C). In method (5), it is preferred that component (A) is first supplied to the system, and a mixture solution containing component (B') and component (C) is supplied to the system in the presence of component (A).

In the process of the present invention (Invention I and Invention II), other conventional polymerization inhibitors, such as phenolic polymerization inhibitors such as hydroquinone, methoquinone (p-methoxyphenol), p-t-butylcatechol, and t-butylhydroquinone, and phenothiazine, can be added where desired in order to further enhance the effect of inhibiting polymerization.

The process of the present invention is applied to inhibition of polymerization of a vinyl compound, and the mode of the application is not particularly limited. For example, the process can be applied to storage of a vinyl compound in a tank, or to a production process of a vinyl compound. Among these modes of application, the application to a production process of a vinyl compound, preferably to a distillation process, is advantageous. Particularly when one or both of N-nitrosophenylhydroxylamine and a salt thereof are present in combination with copper dibutyldithiocarbamate in a distillation process of acrylic acid or methacrylic acid, polymerization of acrylic acid or methacrylic acid is effectively inhibited in both of parts of the liquid phase and parts formed by condensation of the gaseous phase. Moreover, corrosion of the apparatus can effectively be prevented by the presence of at least one selected from the group consisting of inorganic acids, salts of inorganic acids, and water in combination with the above compounds. Thus, the production process can be conducted with stability for a long time.

In the process of the present invention, the temperature of treatment of the vinyl compound containing component (A) and component (B) or the vinyl compound containing component (A), component (B'), and component (C) is different depending on the type of the vinyl compound, and is generally in the range of 0° to 200° C., preferably in the range of 50° to 140° C. The pressure of treatment is not particularly limited, and a treatment may be conducted under a reduced pressure or under an added pressure. The pressure is generally in the range of 0 to 10 MPa. Particularly when acrylic acid or methacrylic acid is distilled, the distillation is generally conducted under a reduced pressure, and the pressure is preferably in the range of 0.01 to 0.1 MPa.

The present invention is described in more detail with reference to examples. However, the present invention is not limited by the examples.

EXAMPLE 1

To 300 g of acrylic acid, 0.03 g of copper dibutyldithiocarbamate as polymerization inhibitor I was added and dissolved at a room temperature. To the prepared solution, 0.03 g of ammonium salt of N-nitrosophenylhydroxylamine as polymerization inhibitor II was added and dissolved at a room temperature.

The solution prepared above was placed in a 500 ml flask. A column having a diameter of 2.54 cm and a height of 30 cm was packed with glass beads having a diameter of 5 mm. The packed column was attached to the above flask, and the content of the flask was refluxed under the condition of 90° C., 110 Torr. During the refluxing, nitrogen gas was introduced into the solution at a rate of 1 $cm^3$/min. The time passed from the start of the refluxing before the column packed with the glass beads was choked by the formation of polymer was measured. The results are shown in Table 1. No polymerization was observed in the part of the liquid phase.

EXAMPLES 2 to 4 AND COMPARATIVE EXAMPLES 1 to 9

The same procedures as those conducted in Example 1 were conducted except that polymerization inhibitors of the types and the amounts shown in Table 1 were used, and a gas of the type and the amount also shown in Table 1 was introduced. The time passed from the start of the refluxing before the column packed with the glass beads was choked by the formation of polymer was measured. The presence or the absence of polymerization in the part of the liquid phase was confirmed. The results are shown in Table 1.

TABLE 1-1

| | polymerization inhibitor I | | polymerization inhibitor II | | introduced gas | |
|---|---|---|---|---|---|---|
| | type | amount (ppm by wt.) | type | amount (ppm by wt.) | type | amount ($cm^3$/min) |
| Example 1 | CuDTC | 100 | NPH | 100 | $N_2$ | 1 |
| Example 2 | CuDTC | 100 | NPH | 10 | $N_2$ | 1 |
| Example 3 | CuDTC | 100 | NPH | 5 | $N_2$ | 1 |
| Example 4 | Cu acetate | 40 | NPH | 10 | $N_2$ | 1 |
| Comparative Example 1 | CuDTC | 100 | — | — | $N_2$ | 1 |
| Comparative Example 2 | CuDTC | 100 | MQ | 100 | $N_2$ | 1 |
| Comparative Example 3 | CuDTC | 100 | CuDTC | 100 | $N_2$ | 1 |

TABLE 1-1-continued

| | polymerization inhibitor I | | polymerization inhibitor II | | introduced gas | |
|---|---|---|---|---|---|---|
| | type | amount (ppm by wt.) | type | amount (ppm by wt.) | type | amount (cm³/min) |
| Comparative Example 4 | CuDTC | 100 | HQ | 100 | N₂ | 1 |
| Comparative Example 5 | CuDTC | 100 | — | — | Air | 1 |
| Comparative Example 6 | — | — | HQ | 100 | Air | 1 |
| Comparative Example 7 | HQ | 1000 | NPH | 10 | Air | 5 |
| Comparative Example 8 | HQ | 1000 | NPH | 100 | Air | 5 |
| Comparative Example 9 | Mn acetate | 100 | NPH | 100 | N₂ | 1 |

Note:
CuDTC: copper dibutyldithiocarbamate
NPH: ammonium salt of N-nitrosophenylhydroxylamine
HQ: hydroquinone
MQ: methoquinone
Mn acetate: manganese acetate tetrahydrate
ppm by wt.: ppm by weight based on the amount of acrylic acid

TABLE 1-2

| | results | |
|---|---|---|
| | time before choking of column by polymer (min) | polymerization in the part of the liquid phase |
| Example 1 | >480 | absent |
| Example 2 | 300 | absent |
| Example 3 | 255 | absent |
| Example 4 | >480 | absent |
| Comparative Example 1 | 55 | absent |
| Comparative Example 2 | 160 | absent |
| Comparative Example 3 | 55 | absent |
| Comparative Example 4 | 70 | absent |
| Comparative Example 5 | 45 | absent |
| Comparative Example 6 | 25 (polymerization in the part of the liquid phase) | present |
| Comparative Example 7 | 55 | absent |
| Comparative Example 8 | 85 | absent |
| Comparative Example 9 | 45 (polymerization in the part of the liquid phase) | present |

COMPARATIVE EXAMPLE 10

In a 500 ml separable flask equipped with a cooler, a test piece of SUS316 (40×15×3 mm) which had been treated with the oxide film coating and 200 ml of acrylic acid in which 3500 ppm by weight (based on the amount of acrylic acid; the same in the following descriptions) of copper dibutyldithiocarbamate as the polymerization inhibitor had been dissolved were placed. The content of the flask was kept under the refluxing condition for 1 day by keeping the temperature in the flask at 110° C. under a reduced pressure.

The decrease in the weight of the test piece by corrosion (the decrease in the weight expressed as the fraction based on the original weight of the test piece before the test) was found to be 507 ppm by weight. White turbidity by the formation of polymer was not found in the part of the liquid phase in the flask. A large amount of polymer was formed on the lower surface of the upper cap of the flask to which the part formed by condensation of the gaseous phase was attached. The conditions and the results are shown in Table 2.

COMPARATIVE EXAMPLE 11

The same procedures as those conducted in Comparative Example 10 were conducted except that phenothiazine was used as the polymerization inhibitor in place of copper dibutyldithiocarbamate. The conditions and the results are shown in Table 2.

COMPARATIVE EXAMPLE 12

The same procedures as those conducted in Comparative Example 10 were conducted except that 200 ml of acrylic acid, in which 8500 ppm by weight of phosphoric acid was dissolved in addition to 3500 ppm by weight of copper dibutyldithiocarbamate, was used. The conditions and the results are shown in Table 2.

COMPARATIVE EXAMPLE 13

The same procedures as those conducted in Comparative Example 10 were conducted except that 200 ml of acrylic acid, in which 2000 ppm by weight of water was dissolved in addition to 3500 ppm by weight of copper dibutyldithiocarbamate, was used. The conditions and the results are shown in Table 2.

COMPARATIVE EXAMPLE 14

The same procedures as those conducted in Comparative Example 10 were conducted except that 200 ml of acrylic acid, in which 7000 ppm by weight of copper dibutyldithiocarbamate was dissolved, was used. The conditions and the results are shown in Table 2.

COMPARATIVE EXAMPLE 15

The same procedures as those conducted in Comparative Example 10 were conducted except that 200 ml of acrylic acid, in which 500 ppm by weight of copper dibutyldithiocarbamate was dissolved, was used. The conditions and the results are shown in Table 2.

COMPARATIVE EXAMPLE 16

The same procedures as those conducted in Comparative Example 10 were conducted except that 200 ml of acrylic acid, in which 3500 ppm by weight of methoquinone was dissolved in addition to 3500 ppm by weight of copper dibutyldithiocarbamate, was used. The conditions and the results are shown in Table 2.

COMPARATIVE EXAMPLE 17

The same procedures as those conducted in Comparative Example 10 were conducted except that 200 ml of acrylic acid, in which 1000 ppm by weight of phenothiazine, 2000 ppm by weight of hydroquinone, 2000 ppm by weight of methoquinone, and 8500 ppm by weight of phosphoric acid were dissolved in addition to 3500 ppm by weight of copper dibutyldithiocarbamate, was used. The conditions and the results are shown in Table 2.

COMPARATIVE EXAMPLE 18

The same procedures as those conducted in Comparative Example 10 were conducted except that 200 ml of acrylic acid, in which 1000 ppm by weight of phenothiazine, 2000 ppm by weight of hydroquinone, 2000 ppm by weight of methoquinone, and 350 ppm by weight of ammonium salt of N-nitrosophenylhydroxylamine were dissolved in place of copper dibutyldithiocarbamate, was used. The conditions and the results are shown in Table 2.

TABLE 2-1

|  | Comparative Example 10 | Comparative Example 11 | Comparative Example 12 |
|---|---|---|---|
| content, ppm by wt. (based on acrylic acid) |  |  |  |
| copper dibutyldithiocarbamate | 3500 | — | 3500 |
| phenothiazine | — | 3500 | — |
| hydroquinone | — | — | — |
| methoquinone | — | — | — |
| NPH | — | — | — |
| phosphoric acid | — | — | 8500 |
| water | — | — | — |
| decrease in weight of test piece (ppm by wt.; decrease in wt./original wt.) | 507 | 2 | 1 |
| condition in the part of the liquid phase | ○ | Δ | ○ |
| condition in the part formed by condensation of the gaseous phase | X | X | X |

NPH: ammonium salt of N-nitrosophenylhydroxylamine

TABLE 2-2

|  | Comparative Example 13 | Comparative Example 14 | Comparative Example 15 |
|---|---|---|---|
| content, ppm by wt. (based on acrylic acid) |  |  |  |
| copper dibutyldithiocarbamate | 3500 | 7000 | 500 |
| phenothiazine | — | — | — |
| hydroquinone | — | — | — |
| methoquinone | — | — | — |
| NPH | — | — | — |
| phosphoric acid | — | — | — |
| water | 2000 | — | — |
| decrease in weight of test piece (ppm by wt.; decrease in wt./original wt.) | 1 | 1444 | 24 |
| condition in the part of the liquid phase | ○ | ○ | ○ |
| condition in the part formed by condensation of the gaseous phase | X | X | X |

NPH: ammonium salt of N-nitrosophenylhydroxylamine

TABLE 2-3

|  | Comparative Example 16 | Comparative Example 17 | Comparative Example 18 |
|---|---|---|---|
| content, ppm by wt. (based on acrylic acid) |  |  |  |
| copper dibutyldithiocarbamate | 3500 | 3500 | — |
| phenothiazine | — | 1000 | 1000 |
| hydroquinone | — | 2000 | 2000 |
| methoquinone | 3500 | 2000 | 2000 |
| NPH | — | — | 350 |
| phosphoric acid | — | 8500 | — |
| water | — | — | — |
| decrease in weight of test piece (ppm by wt.; decrease in wt./original wt.) | 445 | 1 | 1 |
| condition in the part of the liquid phase | ○ | ○ | Δ |
| condition in the part formed by condensation of the gaseous phase | Δ | Δ | Δ |

NPH: ammonium salt of N-nitrosophenylhydroxylamine
Notes: The condition in the part of the liquid phase was evaluated in accordance with the following criterion:
○: no white turbidity by the formation of polymer found
Δ: slight white turbidity by the formation of polymer found
x: white turbidity by the formation of polymer found
The condition in the part formed by condensation of the gaseous phase was evaluated in accordance with the following criterion:
○: no formation of polymer found on the lower surface of the upper cap of the flask
Δ: slight formation of polymer found on the lower surface of the upper cap of the flask
x: formation of polymer found on the lower surface of the upper cap of the flask By comparing the results in Comparative Example 10 and Comparative Example 12 which are shown in Table 2, it can be understood that copper dibutyldithiocarbamate has the corrosive property. The results in Comparative Examples 10, 11, and 12 show that copper dibutyldithiocarbamate exhibited very poor effect of inhibiting polymerization in the part formed by condensation of the gaseous phase although it exhibited good effect of inhibiting polymerization in the part of the liquid phase. By comparing the results in Comparative Example 10 and those in Comparative Examples 12 and 13, it can be understood that phosphoric acid and water are effective as the agent suppressing corrosion.

EXAMPLE 5

The same procedures as those conducted in Comparative Example 10 were conducted except that 200 ml of acrylic acid, in which 8500 ppm by weight of phosphoric acid was dissolved together with 3500 ppm by weight of copper dibutyldithiocarbamate and subsequently 350 ppm by weight of ammonium salt of N-nitrosophenylhydroxylamine was dissolved, was used. The conditions and the results are shown in Table 3.

When the same procedures as those described above were conducted except that phosphoric acid was not used, an effect of inhibiting polymerization as excellent as that obtained by using phosphoric acid was exhibited in both of the part of the liquid phase and the part formed by condensation of the gaseous phase. However, when phosphoric acid was not used, decrease in the weight of the test piece was as high as 426 ppm by weight (when phosphoric acid was used, the corresponding value was 1 ppm by weight).

EXAMPLE 6

The same procedures as those conducted in Example 5 were conducted except that the used amount of phosphoric acid was decreased to 4000 ppm by weight. The conditions and the results are shown in Table 3.

EXAMPLE 7

The same procedures as those conducted in Example 5 were conducted except that the used amount of phosphoric acid was further decreased to 400 ppm by weight. The conditions and the results are shown in Table 3.

EXAMPLE 8

The same procedures as those conducted in Example 5 were conducted except that the used amount of copper dibutyldithiocarbamate was increased to 7000 ppm by weight. The conditions and the results are shown in Table 3.

EXAMPLE 9

The same procedures as those conducted in Example 5 were conducted except that the used amount of copper dibutyldithiocarbamate was decreased to 500 ppm by weight, the used amount of ammonium salt of N-nitrosophenylhydroxylamine was decreased to 50 ppm by weight, and the used amount of phosphoric acid was decreased to 50 ppm by weight. The conditions and the results are shown in Table 3.

EXAMPLE 10

The same procedures as those conducted in Example 9 were conducted except that the used amount of ammonium salt of N-nitrosophenylhydroxylamine was further decreased to 25 ppm by weight. The conditions and the results are shown in Table 3.

EXAMPLE 11

The same procedures as those conducted in Example 5 were conducted except that 2000 ppm by weight of water was used in place of phosphoric acid. The conditions and the results are shown in Table 3.

EXAMPLE 12

The same procedures as those conducted in Example 5 were conducted except that 2000 ppm by weight of water was additionally used. The conditions and the results are shown in Table 3.

EXAMPLE 13

The same procedures as those conducted in Example 5 were conducted except that 1700 ppm by weight of zinc phosphate was used in place of phosphoric acid. The conditions and the results are shown in Table 3.

EXAMPLE 14

The same procedures as those conducted in Example 9 were conducted except that 1700 ppm by weight of zinc phosphate was used in place of phosphoric acid. The conditions and the results are shown in Table 3.

EXAMPLE 15

The same procedures as those conducted in Example 5 were conducted except that 3300 ppm by weight of boric acid was used in place of phosphoric acid. The conditions and the results are shown in Table 3.

EXAMPLE 16

The same procedures as those conducted in Example 15 were conducted except that 900 ppm by weight of zinc borate and 900 ppm by weight of water were used in place of boric acid. The conditions and the results are shown in Table 3.

EXAMPLE 17

The same procedures as those conducted in Example 5 were conducted except that 200 ml of acrylic acid, in which 1000 ppm by weight of phenothiazine, 2000 ppm by weight of hydroquinone, 2000 ppm by weight of methoquinone, 350 ppm by weight of ammonium salt of N-nitrosophenylhydroxylamine, and 8500 ppm by weight of phosphoric acid were dissolved together with 3500 ppm of copper dibutyldithiocarbamate, was used. The conditions and the results are shown in Table 3.

When the same procedures as those described above were conducted except that phosphoric acid was not used, an effect of inhibiting polymerization as excellent as that obtained by using phosphoric acid was exhibited in both of the part of the liquid phase and the part formed by condensation of the gaseous phase. However, when phosphoric acid was not used, decrease in the weight of the test piece was as high as 442 ppm by weight (when phosphoric acid was used, the corresponding value was 1 ppm by weight).

TABLE 3-1

|  | Example 5 | Example 6 | Example 7 | Example 8 | Example 9 |
|---|---|---|---|---|---|
| content, ppm by wt. (based on acrylic acid) |  |  |  |  |  |
| copper dibutyldithio-carbamate | 3500 | 3500 | 3500 | 7000 | 500 |
| phenothiazine | — | — | — | — | — |
| hydroquinone | — | — | — | — | — |
| methoquinone | — | — | — | — | — |
| NPH | 350 | 350 | 350 | 350 | 50 |
| phosphoric acid | 8500 | 4000 | 400 | 8500 | 50 |
| zinc phosphate | — | — | — | — | — |
| boric acid | — | — | — | — | — |
| zinc borate | — | — | — | — | — |
| water | — | — | — | — | — |
| decrease in weight of test piece (ppm by wt.; decrease in wt./original wt.) | 1 | 4 | 3 | 5 | 6 |
| condition in the part of the liquid phase | ○ | ○ | ○ | ○ | ○ |
| condition in the part formed by condensation of the gaseous phase | ○ | ○ | ○ | ○ | ○ |

NPH: ammonium salt of N-nitrosophenylhydroxylamine
Note: When phosphoric acid was not used in Example 5, the condition was evaluated as ○ in both of the part of the liquid phase and the part formed by condensation of the gaseous phase. However, decrease in the weight of the test piece was 426 ppm by weight.

TABLE 3-2

|  | Example 10 | Example 11 | Example 12 | Example 13 |
|---|---|---|---|---|
| content, ppm by wt. (based on acrylic acid) |  |  |  |  |
| copper dibutyldithio-carbamate | 500 | 3500 | 3500 | 3500 |
| phenothiazine | — | — | — | — |
| hydroquinone | — | — | — | — |
| methoquinone | — | — | — | — |
| NPH | 25 | 350 | 350 | 350 |
| phosphoric acid | 50 | — | 8500 | — |
| zinc phosphate | — | — | — | 1700 |
| boric acid | — | — | — | — |
| zinc borate | — | — | — | — |
| water | — | 2000 | 2000 | — |
| decrease in weight of test piece (ppm by wt.; decrease in wt./original wt.) | 4 | 3 | 1 | 62 |
| condition in the part of the liquid phase | ○ | ○ | ○ | ○ |
| condition in the part formed by condensation of the gaseous phase | ○ | ○ | ○ | ○ |

NPH: ammonium salt of N-nitrosophenylhydroxylamine

TABLE 3-3

| | Example 14 | Example 15 | Example 16 | Example 17 |
|---|---|---|---|---|
| content, ppm by wt. (based on acrylic acid) | | | | |
| copper dibutyldithio-carbamate | 500 | 3500 | 3500 | 3500 |
| phenothiazine | — | — | — | 1000 |
| hydroquinone | — | — | — | 2000 |
| methoquinone | — | — | — | 2000 |
| NPH | 50 | 350 | 350 | 350 |
| phosphoric acid | — | — | — | 8500 |
| zinc phosphate | 1700 | — | — | — |
| boric acid | — | 3300 | — | — |
| zinc borate | — | — | 900 | — |
| water | — | — | 900 | — |
| decrease in weight of test piece (ppm by wt.; decrease in wt./original wt.) | 10 | 11 | 22 | 1 |
| condition in the part of the liquid phase | ○ | ○ | ○ | ○ |
| condition in the part formed by condensation of the gaseous phase | ○ | ○ | ○ | ○ |

NPH: ammonium salt of N-nitrosophenylhydroxylamine
Notes
(1): The conditions in the part of the liquid phase and in the part formed by condensation of the gaseous phase were evaluated in accordance with the criteria described in the note to Table 2.
(2): When phosphoric acid was not used in Example 17, the condition of polymerization was evaluated as ○ in both of the part of the liquid phase and the part formed by condensation of the gaseous phase. However, decrease in the weight of the test piece was 442 ppm by weight.

As can be clearly understood from Table 3, in accordance with the process of the present invention, an excellent effect of inhibiting polymerization was exhibited in both of the part of the liquid phase and the part formed by condensation of the gaseous phase, and corrosion of the test pieces was very small.

INDUSTRIAL APPLICABILITY

In accordance with the process of the present invention, stable continuous operation of a process for producing a vinyl compound, particularly acrylic acid or methacrylic acid, such as a distillation process of the vinyl compound, for a long time is enabled by effectively suppressing polymerization of the vinyl compound in parts of the liquid phase and in parts formed by condensation of the gaseous phase in the process or by effectively suppressing polymerization of the vinyl compound in parts of the liquid phase and in parts formed by condensation of the gaseous phase in the process while corrosion of the apparatus for the production is prevented.

We claim:

1. A process for inhibiting polymerization of a vinyl compound comprising using (A) one or both of N-nitrosophenylhydroxylamine and a salt thereof in combination with (B) a salt of copper and (C) at least one of phosphoric acid, boric acid, salt of phosphoric acid, salt of boric acid or water, said water being present in an amount of 0.05 to 5% by weight based on the amount of vinyl compound.

2. A process for inhibiting polymerization of a vinyl compound according to claim 1 wherein the salt of N-nitrosophenylhydroxylamine of component (A) is ammonium salt of N-nitrosophenylhydroxylamine.

3. A process for inhibiting polymerization of a vinyl compound according to claim 1 wherein the salt of copper of component (B) is copper dibutyldithiocarbamate.

4. A process for inhibiting polymerization of a vinyl compound according to claim 1 wherein the process inhibits polymerization of a vinyl compound in a process for producing the vinyl compound.

5. A process for inhibiting polymerization of a vinyl compound according to claim 1 wherein the process inhibits polymerization of a vinyl compound in a distillation process of the vinyl compound.

6. A process for inhibiting polymerization of a vinyl compound according to claim 1 wherein the vinyl compound is acrylic acid or methacrylic acid.

7. A process for inhibiting polymerization of a vinyl compound comprising using (A) one or both of N-nitrosophenylhydroxylamine and a salt thereof in combination with (B') a metal salt of a dialkyldithiocarbamic acid and (C) at least one of phosphoric acid, boric acid, salt of phosphoric acid, salt of boric acid or water, said water being present in an amount of 0.05 to 5% by weight based on the amount of vinyl compound.

8. A process for inhibiting polymerization of a vinyl compound according to claim 7 wherein the salt of N-nitrosophenylhydroxylamine of component (A) is ammonium salt of N-nitrosophenylhydroxylamine.

9. A process for inhibiting polymerization of a vinyl compound according to claim 7 wherein the metal salt of a dialkyldithiocarbamic acid of component (B') is copper dibutyldithiocarbamate.

10. A process for inhibiting polymerization of a vinyl compound according to claim 7 wherein component (C) is phosphoric acid or boric acid.

11. A process for inhibiting polymerization of a vinyl compound according to claim 7 wherein the process inhibits polymerization of a vinyl compound in a process for producing the vinyl compound.

12. A process for inhibiting polymerization of a vinyl compound according to claim 7 wherein the process inhibits polymerization of a vinyl compound in a distillation process of the vinyl compound.

13. A process for inhibiting polymerization of a vinyl compound according to claim 7 wherein the vinyl compound is acrylic acid or methacrylic acid.

14. A process for inhibiting polymerization of a vinyl compound comprising using a composition consisting essentially of (A) one or both of N-nitrosophenylhydroxylamine and a salt thereof in combination with (B') a metal salt of a dialkyldithiocarbamic acid and (C) at least one member selected from the group consisting of inorganic acids, salts of inorganic acids, and water.

15. A process for inhibiting polymerization of a vinyl compound according to claim 14 wherein the salt of N-nitrosophenylhydroxylamine of component (A) is ammonium salt of N-nitrosophenylhydroxylamine.

16. A process for inhibiting polymerization of a vinyl compound according to claim 14 wherein the metal salt of a dialkyldithiocarbamic acid of component (B') is copper dibutyldithiocarbamate.

17. A process for inhibiting polymerization of a vinyl compound according to claim 14 wherein the inorganic acids for component (C) are phosphoric acid or boric acid.

18. A process for inhibiting polymerization of a vinyl compound according to claim 14 wherein the process inhibits polymerization of a vinyl compound in a process for producing the vinyl compound.

19. A process for inhibiting polymerization of a vinyl compound according to claim 14 wherein the process inhibits polymerization of a vinyl compound in a distillation process of the vinyl compound.

20. A process for inhibiting polymerization of a vinyl compound according to claim 14 wherein the vinyl compound is acrylic acid or methacrylic acid.

21. A process of inhibiting polymerization of a vinyl compound according to claim 14, wherein water is present in an amount of 0.05 to 5% by weight based on the amount of vinyl compound.

* * * * *